United States Patent [19]

Villani

[11] Patent Number: 4,560,688

[45] Date of Patent: Dec. 24, 1985

[54] TRICYCLIC ANTIHISTAMINES

[75] Inventor: Frank J. Villani, West Caldwell, N.J.

[73] Assignee: Schering Corporation, Kenilworth, N.J.

[21] Appl. No.: 578,381

[22] Filed: Feb. 8, 1984

Related U.S. Application Data

[60] Division of Ser. No. 403,274, Jul. 29, 1982, Pat. No. 4,454,143, which is a division of Ser. No. 243,681, Mar. 16, 1981, Pat. No. 4,355,036, which is a continuation-in-part of Ser. No. 160,795, Jun. 19, 1980, Pat. No. 4,282,233.

[51] Int. Cl.[4] .................... A61K 31/53; C07D 253/08
[52] U.S. Cl. .................................. 514/243; 514/248; 514/250; 514/267; 514/322; 514/323; 514/359; 514/393; 514/406; 514/411; 544/183; 544/234; 544/249; 544/344; 546/199; 546/200; 548/257; 548/259; 548/260; 548/261; 548/323; 548/369; 548/427
[58] Field of Search .............. 548/427, 257, 259, 260, 548/261, 323, 369; 546/200, 93, 101, 111, 199; 424/267, 274, 263; 544/183, 234, 249, 344; 514/243, 248, 250, 267, 322

[56] References Cited

U.S. PATENT DOCUMENTS

3,326,924  6/1967  Villani .......................... 546/194 X
3,997,557  12/1976  Helsley et al. ...................... 548/427

OTHER PUBLICATIONS

Chemical Abstracts, 72:90465u, (1970).
Chemical Abstracts, 82:51351r, (1975).
Chemical Abstracts, 82:125317h, (1975).
Chemical Abstracts, 69:18890z, (1968).
Chemical Abstracts, 82:16734w, (1975).
Chemical Abstracts, 82:140188k, (1975).
Chemical Abstracts, 94:47058f, (1981).
Cram, D., et al., Organic Chemistry, McGraw Hill, New York, 1959, p. 487.

*Primary Examiner*—Richard A. Schwartz
*Attorney, Agent, or Firm*—James R. Nelson; Stephen I. Miller

[57] ABSTRACT

Antihistamines of the formula

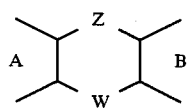

wherein

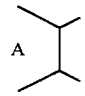

is a 5 or 6 membered ring which is phenyl or heterocyclic;

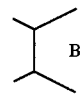

is a six membered ring which is 2,3, or 4 pyridyl or is phenyl or substituted phenyl, with the proviso that is

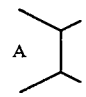

is a nitrogen containing ring,

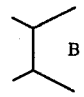

must be phenyl; Z is an alkylene chain having 0 to 2 carbon atoms in the chain, said 2 carbon chain optionally having one double bond, said chain optionally having either a carbonyl oxygen, or a hydroxy group as a substituent; W is

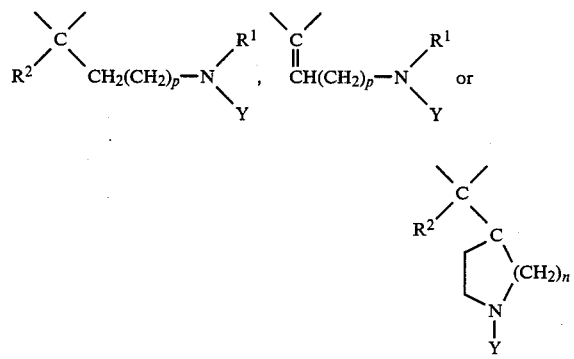

wherein p is 1 or 2 and n is 1 or 2, $R^1$ is $C_1$ to $C_6$ alkyl, $R^2$ is hydrogen or $C_1$ to $C_6$ alkyl, and the dotted line represents an optional double bond, $R^2$ being absent if the double bond is present, and Y is substiuted carboxylate or substituted sulfonyl. Said antihistamines have little or no sedative effects.

10 Claims, No Drawings

TRICYCLIC ANTIHISTAMINES

This application is a division of U.S. Ser. No. 403,274, filed July 29, 1982 now U.S. Pat. No. 4,454,143 which is a division of U.S. Ser. No. 243,681, filed Mar. 16, 1981 now U.S. Pat. No. 4,355,036 which is a continuation-in-part of U.S. Ser. No. 160,795, filed June 19, 1980 now U.S. Pat. No. 4,282,233.

The present invention relates to novel antihistamines.

The compounds of the present invention may be similar in structure to known antihistamines (for example, azatadine, disclosed in U.S. Pat. No. 3,326,924) but are preferred to the starting materials because the present compounds have little or no sedative effects, thus being preferred for use with patients that must operate machinery or automobiles or perform other mental or physical tasks requiring a high level of concentration.

The present invention also relates to a method of reducing and/or eliminating the sedating effects of antihistamines (for example, dialkylaminoalkyl ethers, dialkylaminoalkyl amines and dialkylaminoethylene diamines), by replacing one of the lower alkyl groups on a tertiary amine by a non-basic function, for example, a carboalkoxy or an alkylsulfonyl derivative.

The compounds of the present invention are compounds of the formula

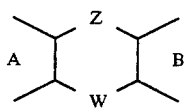

wherein

is a 5 or 6 membered ring which is phenyl or heterocyclic (for example, 2- or 3-thiophene of 2-,3-, or 4-pyridyl);

is a six membered ring which is 2-,3-, or 4-pyridyl or is phenyl or substituted phenyl (for example, phenyl substituted with halo), with the proviso that if

is a nitrogen containing ring,

must be phenyl or substituted phenyl; Z is an alkylene chain having 0 to 2 carbon atoms in the chain, said 2 carbon chain optionally having one double bond, said chain optionally having either a carbonyl oxygen, or a hydroxy group as a substituent; W is

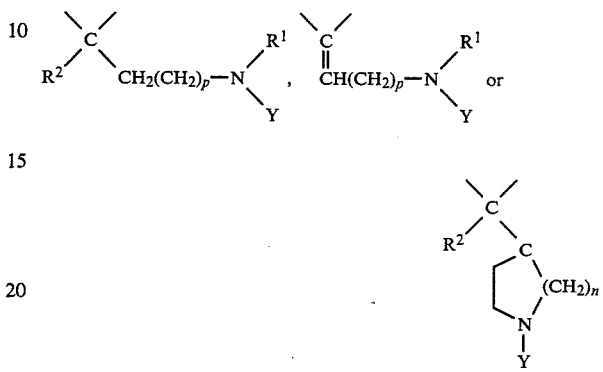

wherein p is 1 or 2 and n is 1 or 2; $R^1$ is $C_1$ to $C_6$ alkyl, $R^2$ is hydrogen or $C_1$ to $C_3$ alkyl, and the dotted line represents an optional double bond, $R^2$ being absent if the double bond is present, an Y is substituted carboxylate or substituted sulfonyl. Preferably, Y is —COOR or —SO$_2$R, with the proviso that when Y is —COOR, R is $C_1$ to $C_{12}$ alkyl, substituted $C_1$ to $C_{12}$ alkyl, $C_2$ to $C_{12}$ alkenyl, more preferably $C_2$ to $C_6$ alkenyl, substituted $C_2$ to $C_{12}$ alkenyl, more preferably substituted $C_2$ to $C_6$ alkenyl phenyl, substituted phenyl, $C_7$ to $C_{10}$ phenylalkyl or $C_7$ to $C_{10}$ phenylalkyl wherein the phenyl moiety is substituted, or R is -2, -3, or -4 piperidyl or N-substituted piperidyl, wherein the substituents on said substituted $C_1$ to $C_{12}$ alkyl and on said substituted $C_2$ to $C_{12}$ alkenyl are selected from amino or substituted amino and the substituents on said substituted amino are selected from $C_1$ to $C_6$ alkyl, the substituents on said substituted phenyl and on said substituted phenyl moiety of the $C_7$ to $C_{10}$ phenylalkyl are selected from $C_1$ to $C_4$ alkyl and halo, and the substituent on said N-substituted piperidyl is $C_1$ to $C_4$ alkyl, and with the proviso that when Y is —SO$_2$R, R is $C_1$ to $C_{12}$ alkyl, $C_2$ to $C_{12}$ alkenyl, more preferably $C_2$ to $C_6$ alkylene, phenyl, substituted phenyl, $C_7$ to $C_{10}$ phenylalkyl, $C_7$ to $C_{10}$ phenylalkyl wherein the phenyl moiety is substituted, wherein the substituents on said substituted phenyl and said substituted phenyl moiety of the $C_7$ to $C_{10}$ phenylalkyl are selected from $C_1$ to $C_4$ alkyl and halo.

Preferably, when Y is —COOR, R is $C_1$ to $C_{12}$ alkyl or substituted alkyl, more preferably, R is $C_1$ to $C_6$ alkyl or substituted alkyl, and most preferably R is $C_1$ to $C_6$ alkyl.

Preferably, when Y is —SO$_2$R, R is $C_1$ to $C_{12}$ alkyl, more preferably $C_1$ to $C_6$ alkyl.

In a preferred embodiment, the compounds of the present invention are compounds of the formula

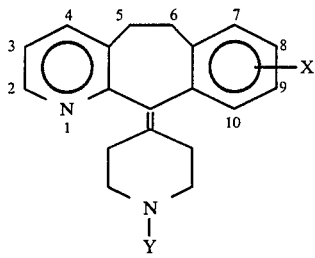

wherein the dotted line represents an optional double bond and wherein the numbering system used herein for these preferred compounds is illustrated. In this formula, X is hydrogen or halo and Y is substituted carboxylate or substituted sulfonyl. Preferably, Y is —COOR or —$SO_2R$, with the proviso that when Y is —COOR, R is $C_1$ to $C_{12}$ alkyl, substituted $C_1$ to $C_{12}$ alkyl, $C_2$ to $C_{12}$ alkenyl, more preferably $C_2$ to $C_6$ alkylene, substituted $C_2$ to $C_{12}$ alkenyl, more preferably substituted $C_2$ to $C_6$ alkenyl, phenyl, substituted phenyl, $C_7$ to $C_{10}$ phenylalkyl or $C_7$ to $C_{10}$ phenylalkyl wherein the phenyl moiety is substituted or R is -2, -3, or -4 piperidyl or N-substituted piperidyl, wherein the substituents on said substituted $C_1$ to $C_{12}$ alkyl and on said substituted $C_2$ to $C_{12}$ alkenyl are selected from amino or substituted amino and the substituents on said substituted amino are selected from $C_1$ to $C_6$ alkyl, the substituents on said substituted phenyl and on said substituted phenyl moiety of the $C_7$ to $C_{10}$ phenylalkyl are selected from $C_1$ to $C_4$ alkyl and halo, and the substituent on said N-substituted piperidyl is $C_1$ to $C_4$ alkyl; and with the proviso that when Y is —$SO_2R$, R is $C_1$ to $C_{12}$ alkyl, $C_2$ to $C_{12}$ alkenyl, more preferably $C_2$ to $C_6$ alkenyl, phenyl, substituted phenyl, $C_7$ to $C_{10}$ phenylalkyl, $C_7$ to $C_{10}$ phenylalkyl wherein the phenyl moiety is substituted, wherein the substituents on said substituted phenyl and said substituted phenyl moiety of the $C_7$ to $C_{10}$ phenylalkyl are selected from $C_1$ to $C_4$ alkyl an halo.

Preferably, when Y is —COOR, R is $C_1$ to $C_{12}$ alkyl or substituted alkyl, more preferably, R is $C_1$ to $C_6$ alkyl or substituted alkyl, and most preferably R is $C_1$ to $C_6$ alkyl.

Preferably, when Y is —$SO_2R$, R is $C_1$ to $C_{12}$ alkyl, more preferably $C_1$ to $C_6$ alkyl.

The aforementioned alkyl groups in formula I and formula II may be linear, branched or cyclic or may contain both cyclic and linear or cyclic and branched moieties. Halo may be fluoro, chloro, bromo or iodo.

The present invention also relates to a pharmaceutical composition comprising an effective amount of a compound of the formula I as defined above, together with a pharmaceutically acceptable carrier and to a method of effecting an antiallergic response in an animal comprising administering to the animal an effective amount of the formula I as defined above.

Generally, compounds of the present invention are prepared by replacing a methyl or another replaceable substituent, for example carbophenoxy, on the nitrogen of an appropriate compound of the formula I with the desired substituent.

For example, compounds of the formula I wherein Y is —COOR are prepared by reacting a compound of the formula I wherein Y is methyl (Compound IA) or an appropriate derivative of Compound IA with an appropriate chloroformate, for example, an alkylchloroformate or phenyl chloroformate, in order to replace the N-methyl group of Compound IA.

Compounds of the formula I wherein Y is —COOR may also be prepared by reacting a compound of the formula I wherein Y is —COOR and R is phenyl with the sodium salt of an appropriate alcohol.

Compounds of the formula I wherein Y is —COOR may also be prepared by reacting a compound of the formula I wherein Y is —COOR and R is phenyl with the sodium salt of an appropriate alcohol.

Compounds of the formula I wherein Y is —COOR and R is tert-butyl may be prepared by reacting a compound of the formula I wherein Y is hydrogen with a di-tertiarybutyl carbonate in an inert solvent, for example, tetrahydrofuran.

Compounds of the formula I wherein Y is —$SO_2R$ are prepared by reacting a compound of the formula I wherein Y is hydrogen with a compound of the formula Cl—$SO_2R$, wherein R has the same value as R in the desired product, in the presence of an excess of anhydrous potassium carbonate in an inert solvent, for example dry toluene.

It is also contemplated that compounds containing an asymmetric center (for example, position 11 in formula II) may be resolved into their optical isomers (d and l) by methods well-known in the art.

The following non-limiting Examples further illustrate the preparation of the compounds of the present invention:

EXAMPLE 1

A.

11-(N-Carboethoxy-4-piperidylidene)-6,11-dihydro-5H-benzo-[5,6]-cyclohepta-[1,2-b]-pyridine To a solution of 10.9 g (0.1 mole) of ethylchloroformate in 300 ml of anhydrous benzene is added dropwise, with stirring at room temperature, a solution of 14.5 g (0.05M) of 11-(N-methyl-4-piperidylidene)-6,11-dihydro-5H-benzo-[5,6]-cyclohepta-[1,2-b]-pyridine (hereinafter referred to as Compound IA) in 200 ml of benzene. The solution is stirred and is heated under reflux overnight (16-20 hrs.). The mixture is cooled and is poured into ice water and the organic layer is separated, washed with water, dried, and then concentrated to dryness. The residue is triturated with petroleum ether and a white solid having a melting point of 106°-107° C. is recrystallized from isopropyl ether after decolorization with decolorizing carbon.

B.

11-(N-Carboethoxy-4-piperidylidene)-8-chloro-6,11-dihydro-5H-benzo-[5,6]-cyclohepta-[1,2-b]-pyridine Using the procedure of Example IA, react 16.2 g of the 8-chloro derivative of Compound IA and 10.9 g (0.1 mole) of ethylchloroformate to prepare the title compound, having a melting point of 128°-130° C. The 7,9 and 10-chloro analogues are similarly prepared.

C.

11-(N-Carbomethoxy-4-piperidylidene)-6,11-dihydro-5H-benzo-[5,6]-cyclohepta-[1,2-b]-pyridine Using the procedure of Example IA, react 14.5 g of Compound IA and 9.4 g of methylchloroformate to prepare the title compound, having a melting point of 116°-118° C.

D.
11-(β-N-Methyl-N-carboethoxy)ethyl-8-chloro-6,11-dihydro-5H-benzo-[5,6]-cyclohepta-[1,2-b]-pyridine Using the procedure of Example IA react a solution of 15.1 g (0.05 mole) of 11-(-dimethylaminoethyl)-8-chloro-6,11-dihydro-5H-benzo-[5,6]-cyclohepta-[1,2-b]-pyridine in 300 ml of anhydrous benzene with 10.9 g of ethylchloroformate at room temperature to prepare the title compound.

E.
11-(β-N-Methyl-N-carbethoxy)ethylidene-6,11-dihydro-[5H]-benzo-[5,6]-cyclohepta-[1,2-b]-pyridine Prepare the title compound by the procedure of Example IA using 14.9 g of dimethylamino ethylidine-6,11-dihydro-[5H]-benzo-[5,6]-cyclohepta-[1,2-b]-pyridine and 10.9 g of ethylchloroformate at room temperature in benzene.

F.
4-(N-Carboethoxy-piperidylidene)4H-benzo[4,5]-cyclohepta [1,2-b]-thiophene-10(9H)-one Using the procedure of Example IA, react 21.3 g of N-methylpiperidylidene-4H-benzo-[4,5]-cyclohepta-[1,2-b]-thiophene-10(9H)-one in 300 ml of benzene with a solution of 10.9 g of ethylchloroformate in 300 ml benzene to prepare the title compound.

EXAMPLE 2

11-(N-Carbophenoxy-4-piperidylidene)-6,11-dihydro-5H-benzo-[5,6]-cyclohepta-[1,2-b]-pyridine (Compound IB)

To a solution of 29.1 g (0.1 mole) of Compound IA in 150 ml of anhydrous carbon tetrachloride is added 17 g of phenylchloroformate in an equal volume of anhydrous carbontetrachloride. Heat under reflux for 15 minutes with stirring and pour into water. Separate and wash the organic layer with water and remove solvent. Extract the residue with ether, filter off the insoluble material and remove the ether. The residue is recrystallized from isopropyl ether to yield the title compound having a melting point of 127°–130° C. Similarly, prepare the 7,8,9, or 10-chloro derivatives of the title compound using this procedure.

EXAMPLE 3

11-(N-Carboisopropoxy-4-piperidylidene)-6,11-dihydro-5H-benzo-[5,6]-cyclohepta-[1,2-b] pyridine Dissolve 0.5 g sodium metal in 50 ml isopropanol and add 7.9 g of Compound IB from Example 2. Heat with stirring for 5 hours on the steam bath at 90°–95° and allow to cool overnight.

Add ice water to precipitate the product and extract 3 times with ether and once with chloroform. Wash with water, distill off solvents, triturate with hexane and recrystallize from isopropylether. The melting point is 147°–148° C.

Using this procedure, and replacing the isopropanol with n-butanol, cyclopentanol, allyl alcohol, cyclopropylmethanol, benzylalcohol, p-chlorobenzylalcohol, phenethylalcohol, dimethylaminoethylalcohol or N-methyl-4-hydroxy piperidine prepare the corresponding carbamoyl derivatives. Similarly, using the chloro derivatives of Compound IB and the sodium salts of the aforementioned alcohols, prepare the chloro derivatives of the aforementioned carbamoyl derivatives.

EXAMPLE 4

11-(N-Carbo-t-butoxy-4-piperidylidene-6,11-dihydro-5H-benzo-[5,6]-cyclohepta-[1,2b]-pyridine Dissolve 13.8 g of 11-(4-piperidylene)-6,11-dihydro-5H-benzo-[5,6]-cyclohepta-[1,2-b]-pyridine (Compound IC), prepared according to the method of Villani et. al., J. Med. Chem. 15, 750 (1972), in 250 ml of dry tetrahydrofuran. With stirring, add in one portion 12 g of di-butyl carbonate and stir at room temperature overnight. The mixture is poured into water, is extracted with ether and is washed with water and the solvent is removed. Recrystallize the residue from ispropyl ether. The melting point is 144°–145° C.

EXAMPLE 5

N-Methanesulfonyl-4-piperidylidene-6,11-dihydro-5H-benzo-[5,6]-cyclohepta-[1,2-b]-pyridine To 10 g of Compound IC in 200 ml of dry toluene add 13 g of anhydrous potassium carbonate. After several minutes of stirring at room temperature, add dropwise a solution of 6 g of methanesulfonyl chloride in 20 ml of toluene. Continue stirring for 16 to 20 hours and then filter. Recrystallize the solid material from ethanol. The melting point is 223°–224° C.

Using this procedure and adjusting the weight of the requisite sulfonyl chloride so that 0.04 moles of said alkanesulfonyl chloride are used, the ethanesulfonyl, n-propylsulfonyl, n-butylsulfonyl, cyclopropylsulfonyl, heptylsulfonyl, dodecylsulfonyl, phenylsulfonyl, p-methylphenyl-sulfonyl, p-fluorophenylsulfonyl, p-chlorophenylsulfonyl, benzylsulfonyl, p-chlorobenzylsulfonyl, p-tertbutylphenylsulfonyl and cyclopentylsulfonyl compounds of formula I wherein Y is $SO_2R$ are obtained.

Similarly, prepare the tricyclic ring substituted chloro derivatives.

Substituting the appropriate starting material having a double bond between the 5 and 6 positions of the ring system, and using the procedures set forth in Examples 1 to 5 above (which show the preparation of the 6,11-dihydro compounds), the corresponding 6,11-dehydro compounds are prepared.

Also, by substituting an appropriate bromo or other halo analogue for the chloro substituted starting material mentioned above, other desired halo compounds of the Formula I may be prepared.

The compounds of the present invention are useful as non-sedating antihistamines. These compounds act as antiallergic agents in the treatment of such conditions as perennial and seasonal allergic rhinitis and chronic urticaria.

The compounds of the present invention are administered in pharmaceutical formulations comprising the compound in admixture with a pharmaceutical carrier suitable for enteral or parenteral administration. The formulations may be in solid form, as for example tablets and capsules, or in liquid form as for example syrups, elixirs, emulsions, and injectables. In the formulation of pharmaceutical dosage forms there generally is utilized excipients, for example, water, gelatin, lactose, starches, magnesium stearate, talc, vegetable oils, benzyl alcohols, gums, polyalkylene glycols, and petroleum jelly. Preferred formulations are more fully illustrated in Example 6.

The compounds of the present invention are administered in pharmaceutical formulations comprising the compound in admixture with a pharmaceutical carrier suitable for enteral or parenteral administration. The formulations may be in solid form, for example tablets and capsules, or in liquid form, for example syrups, elixirs, emulsions, and injectables. In the formulation of pharmaceutical dosage forms there generally is utilized excipients, for example, water, gelatin, lactose, starches, magnesium stearate, talc, vegetable oils, benzyl alcohols, gums, polyalkylene glycols, and petroleum jelly. Preferred formulations are more fully illustrated in Example 6.

Although the required dosage will be determined by such factors as the patient's age, sex, weight and the severity of the allergic reaction to be treated, the preferred human dosage range is likely to be 4 to 50 mg of the effective compound 1 to 3 times per day. The preferred dosage ranges for other animals can readily be determined by using standard testing methods.

The following Examples are illustrative of the aforementioned pharmaceutical compositions:

EXAMPLE 6

A syrup comprising a compound of the present invention (Active Compound), e.g. 11-(N-carboethoxy-4-piperidylidene)-8-chloro-6,11-dihydro-5H-benzo-[5,6]-cyclohepta-[1,2-b]-pyridine, 11-(N-methanesulfonyl-4-piperidylidene)-6,11-dihydro-5H-benzo-[5,6]-cyclohepta-[1,2-b]-pyridine, 11-(N-carboethoxy-4-piperidylidene)-6,11-dihydro-5H-benzo-5,6]-cyclohepta-[1,2-b]-pyridine, 11-(N-carbomethoxy-4-piperidylidene)-6,11-dihydro-5H-benzo-[5,6]-cyclohepta-[1,2-b]-pyridine or 11-(N-carbophenoxy-4-piperidylidene)-6,11-dihydro-5H-benzo-[5,6-cyclohepta-[1,2-b]-pyridine, is prepared from the following ingredients:

|  | per ml |
| --- | --- |
| Active Compound | 0.100 mg |
| Sucrose | 600 mg |
| Sorbitol | 140 mg |
| Propylene Glycol | 20.0 mg |
| Methylparaben | 1.00 mg |
| Propylparaben | 0.200 mg |
| F.D. & C. Yellow No. 6 | 0.225 mg |
| Alcohol USP | 0.0021 ml |
| Limitation Black Currant Flavor | 0.001 ml |
| Purified Water USP | q.s. |
|  | 1.0 ml |

The syrup is prepared by combining the above ingredients according to standard techniques.

EXAMPLE 7

A tablet comprising a compound of the present invention (Active Compound) is prepared by a spray-dry process from the following ingredients:

|  | mg/tablet |
| --- | --- |
| Component I |  |
| Active Compound | 1.00 |
| Lactose, Hydrous USP (Impalpable Powder) | 212 |
| Povidone NF | 10.0 |
| Corn Starch (Food Grade) | 15.0 |
| Purified Water USP (Evaporates) | 0.102 ml |
| Additional Components |  |
| Corn Starch (Food Grade) | 11.5 |

|  | mg/tablet |
| --- | --- |
| Magnesium Stearate USP | 0.500 |

The materials of Component I are combined and spray dried by standard techniques. The resulting spray dried material is combined with the additional components listed above and processed to form tablets.

I claim:

1. A compound of the formula

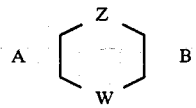

wherein

A 

is a 5 or 6 membered ring which is an aromatic nitrogen heterocycle exclusive of pyridine;

is ortho-phenylene or halo-substituted ortho-phenylene; Z is a bond or an alkylene chain of up to 2 carbon atoms in the chain, said 2 carbon chain optionally having one double bond, said chain optionally having either a carbonyl oxygen, or a hydroxy group as a substituent; W is

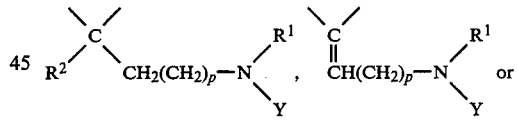

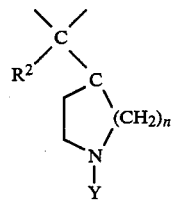

wherein n is 1 or 2 and p is 1 or 2, $R^1$ is $C_1$ to $C_6$ alkyl, $R^2$ is hydrogen or $C_1$ to $C_3$ alkyl, and the dotted line represents an optional double bond, $R^2$ being absent if the double bond is present, and Y is substituted carboxylate or substituted sulfonyl.

2. A compound according to claim 1, wherein Y is —COOR or —SO$_2$R, with the proviso that when Y is —COOR, R is $C_1$ to $C_{12}$ alkyl, substituted $C_1$ to $C_{12}$ alkyl, $C_2$ to $C_{12}$ alkenyl, substituted $C_2$ to $C_{12}$ alkenyl, phenyl, substituted phenyl, $C_7$ to $C_{10}$ phenylalkyl or $C_7$ to $C_{10}$ phenylalkyl wherein the phenyl moiety is substituted, or R is —2, —3, or —4 piperidyl or N-substituted piperidyl, wherein the substituents on said substituted $C_1$ to $C_{12}$ alkyl and on said substituted $C_2$ to $C_{12}$ alkenyl are selected from amino or substituted amino and the substituents on said substituted amino are selected from $C_1$ to $C_6$ alkyl, the substituents on said substituted phenyl and on said substituted phenyl moiety of the $C_7$ to $C_{10}$ phenylalkyl are selected from $C_1$ to $C_4$ alkyl and halo, and the substituent on said N-substituted piperidyl is $C_1$ to $C_4$ alkyl, and with the proviso that when Y is —$SO_2R$, R is $C_1$ to $C_{12}$ alkyl, $C_2$ to $C_{12}$ alkenyl, phenyl, substituted phenyl, $C_7$ to $C_{10}$ phenylalkyl, $C_7$ to $C_{10}$ phenylalkyl wherein the phenyl moiety is substituted, wherein the substituents on said substituted phenyl and said substituted phenyl moiety of the $C_7$ to $C_{10}$ phenylalkyl are selected from $C_1$ to $C_4$ alkyl and halo.

3. A compound according to claim 1, wherein Y is —COOR, wherein R is as defined in claim 27, A is a 6-membered ring said compound having a single bond between the two bridge carbons of the 7-membered ring.

4. A compound according to claim 1, wherein Y is —$SO_2R$, wherein R is as defined in claim 27, A is a 6-membered ring said compound having a single bond between the two bridge carbons of the 7-membered ring.

5. A compound according to claim 3, wherein

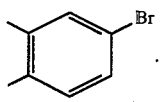

represents an ortho-phenylene radical.

6. A compound according to claim 3, wherein

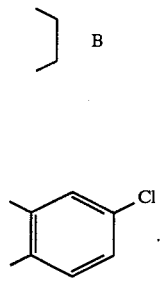

represents

7. A compound according to claim 3, wherein represents

8. A compound according to claim 1, wherein represents an ortho-phenylene radical.

9. An anti-allergic pharmaceutical composition which comprises an effective amount of a compound as defined in claim 1 in combination with a pharmaceutically acceptable carrier.

10. A method of effecting an anti-allergic response in an animal in need of such treatment comprising administering to the animal an effective amount of a compound as defined in claim 1.

* * * * *